US008322340B2

(12) United States Patent
Talmon

(10) Patent No.: US 8,322,340 B2
(45) Date of Patent: Dec. 4, 2012

(54) AIR FILTER FOR ENDONASAL USE

(76) Inventor: Emilio Talmon, Canazei (IT)

( * ) Notice: Subject to any disclaimer, the term of this patent is extended or adjusted under 35 U.S.C. 154(b) by 670 days.

(21) Appl. No.: 12/514,654

(22) PCT Filed: Dec. 29, 2006

(86) PCT No.: PCT/IT2006/000882
§ 371 (c)(1),
(2), (4) Date: May 13, 2009

(87) PCT Pub. No.: WO2008/068788
PCT Pub. Date: Jun. 12, 2008

(65) Prior Publication Data

US 2010/0043799 A1 Feb. 25, 2010

(30) Foreign Application Priority Data

Dec. 5, 2006 (IT) .............................. MI2006A2334

(51) Int. Cl.
*A62B 7/10* (2006.01)
*A61G 10/00* (2006.01)
*A61M 16/00* (2006.01)
*A61F 9/00* (2006.01)

(52) U.S. Cl. .................................. 128/206.11; 128/858

(58) Field of Classification Search .................. 128/858, 128/863, 201.25, 207.13, 205.27, 205.29, 128/206.11
See application file for complete search history.

(56) References Cited

U.S. PATENT DOCUMENTS 701,538 A * 6/1902 Carence .................. 128/204.12
810,617 A * 1/1906 Carence .................. 128/206.11
855,573 A * 6/1907 Heath ...................... 128/206.11
2,046,664 A * 7/1936 Weaver .................... 128/206.11
2,097,846 A * 11/1937 Strauch .................... 128/204.13
2,198,959 A 4/1940 Clarke
2,237,954 A * 4/1941 Wilson ..................... 128/204.12
2,241,472 A * 5/1941 Nemon .................... 128/206.11
2,264,153 A * 11/1941 Rowe ....................... 128/204.12
2,277,390 A * 3/1942 Crespo .................... 128/204.12
2,282,681 A 5/1942 Stotz
(Continued)

FOREIGN PATENT DOCUMENTS

CN 2822687 Y 10/2006
(Continued)

OTHER PUBLICATIONS

International Search Report dated Jul. 31, 2007, from corresponding PCT application.

*Primary Examiner* — Loan Thanh
*Assistant Examiner* — Sandhara Ganesan
(74) *Attorney, Agent, or Firm* — Young & Thompson

(57) ABSTRACT

A description is given of an endonasal filter including two essentially planar filtering components joined at their respective ends by a flexible element mounted, similar to a spring, across the cartilage between the two nostrils. The shape of the filtering components is that of a lunette as is the shape of the section at entry to the channel communicating with the nasal cavities. The filtering components are joined by a thin piece of plastic shaped to form a U-bend, the two parallel sides of which extend towards the filtering components on whose surfaces they assume the form of an oval that supports the component and to which it is made to adhere by application of heat.

7 Claims, 1 Drawing Sheet

U.S. PATENT DOCUMENTS

| | | | | | |
|---|---|---|---|---|---|
| 2,433,565 | A | * | 12/1947 | Korman | 128/204.12 |
| 2,535,155 | A | * | 12/1950 | Pandorf | 128/204.12 |
| 2,672,138 | A | * | 3/1954 | Carlock | 128/207.18 |
| 2,890,695 | A | * | 6/1959 | Safstrom | 128/206.11 |
| 3,145,711 | A | * | 8/1964 | Beber | 128/204.12 |
| 3,457,917 | A | * | 7/1969 | Mercurio | 128/204.12 |
| 3,463,149 | A | * | 8/1969 | Albu | 128/204.12 |
| 3,722,509 | A | * | 3/1973 | Nebel | 128/204.12 |
| 3,747,597 | A | * | 7/1973 | Olivera | 128/206.11 |
| 3,774,601 | A | * | 11/1973 | Langone | 128/205.29 |
| 3,802,426 | A | * | 4/1974 | Sakamoto | 128/206.11 |
| 3,884,223 | A | * | 5/1975 | Keindl | 128/206.11 |
| 3,905,335 | A | * | 9/1975 | Kapp | 128/206.11 |
| 4,030,491 | A | * | 6/1977 | Mattila | 128/206.11 |
| 4,220,150 | A | * | 9/1980 | King | 128/206.11 |
| 4,267,831 | A | * | 5/1981 | Aguilar | 128/203.14 |
| 4,327,719 | A | * | 5/1982 | Childers | 128/206.11 |
| 4,573,461 | A | * | 3/1986 | Lake | 128/201.18 |
| 4,984,302 | A | * | 1/1991 | Lincoln | 2/206 |
| D319,878 | S | * | 9/1991 | Holland | D24/106 |
| D335,921 | S | * | 5/1993 | Brake | D23/365 |
| 5,392,773 | A | * | 2/1995 | Bertrand | 128/206.11 |
| 5,417,205 | A | * | 5/1995 | Wang | 128/206.11 |
| 5,425,359 | A | * | 6/1995 | Liou | 128/206.11 |
| 5,468,488 | A | * | 11/1995 | Wahi | 424/78.03 |
| 5,485,836 | A | * | 1/1996 | Lincoln | 128/206.11 |
| 5,568,808 | A | * | 10/1996 | Rimkus | 128/206.11 |
| 5,740,798 | A | * | 4/1998 | McKinney | 128/206.18 |
| 5,746,200 | A | * | 5/1998 | Draenert | 128/206.11 |
| 5,787,884 | A | * | 8/1998 | Tovey | 128/206.11 |
| 5,890,491 | A | * | 4/1999 | Rimkus | 128/206.11 |
| 6,098,624 | A | * | 8/2000 | Utamaru | 128/206.18 |
| 6,119,690 | A | * | 9/2000 | Pantaleo | 128/206.11 |
| 6,213,121 | B1 | * | 4/2001 | Cardarelli | 128/206.18 |
| 6,216,694 | B1 | * | 4/2001 | Chen | 128/206.11 |
| D461,890 | S | * | 8/2002 | Lawrence | D24/106 |
| 6,494,205 | B1 | * | 12/2002 | Brown | 128/206.11 |
| 6,562,057 | B2 | * | 5/2003 | Santin | 606/199 |
| 6,564,800 | B1 | * | 5/2003 | Olivares | 128/206.11 |
| 6,701,924 | B1 | * | 3/2004 | Land et al. | 128/206.11 |
| 6,971,388 | B1 | * | 12/2005 | Michaels | 128/206.11 |
| 7,156,099 | B1 | * | 1/2007 | Jenkins | 128/206.11 |
| 2003/0106556 | A1 | * | 6/2003 | Alperovich et al. | 128/206.11 |
| 2003/0144684 | A1 | * | 7/2003 | Ogle | 606/199 |
| 2004/0147954 | A1 | * | 7/2004 | Wood | 606/199 |
| 2004/0261798 | A1 | * | 12/2004 | Rimkus | 128/206.11 |
| 2005/0051170 | A1 | * | 3/2005 | Koo | 128/206.11 |
| 2005/0121036 | A1 | * | 6/2005 | Tohara | 128/207.18 |
| 2005/0161046 | A1 | * | 7/2005 | Michaels | 128/206.14 |
| 2005/0205095 | A1 | * | 9/2005 | Dolezal et al. | 128/206.11 |
| 2006/0032196 | A1 | * | 2/2006 | Moss et al. | 54/80.3 |
| 2007/0227542 | A1 | * | 10/2007 | Kashmakov et al. | 128/206.11 |

FOREIGN PATENT DOCUMENTS

| | | | |
|---|---|---|---|
| DE | 668395 | | 12/1938 |
| DE | 89 10 651 | | 11/1989 |
| EP | 1818079 | A1 | 8/2007 |
| FR | 2594033 | A1 | 8/1987 |
| JP | 3123780 | U | 7/2006 |
| RU | 2130790 | C1 | 5/1999 |
| RU | 2166341 | C1 | 5/2001 |
| WO | 2005/120645 | | 12/2005 |

* cited by examiner

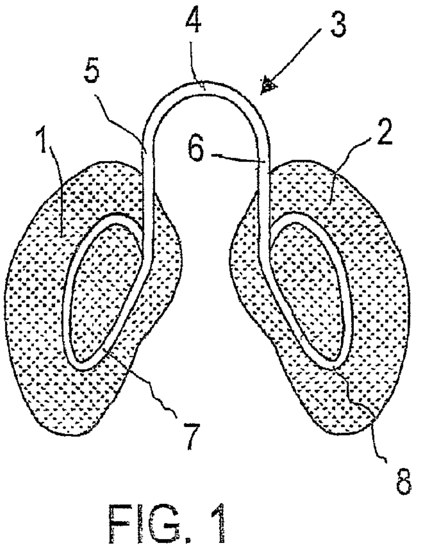
FIG. 1
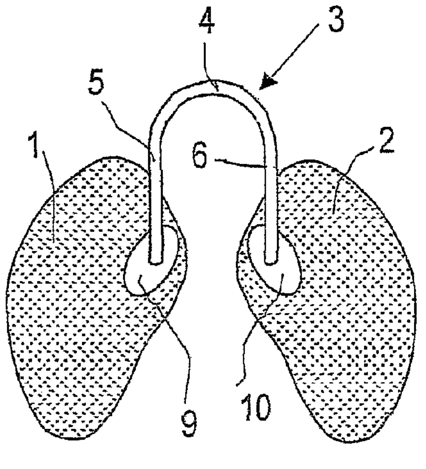
FIG. 2
FIG. 4
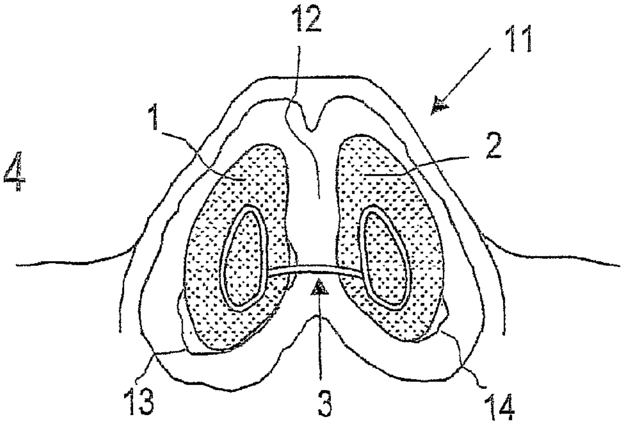
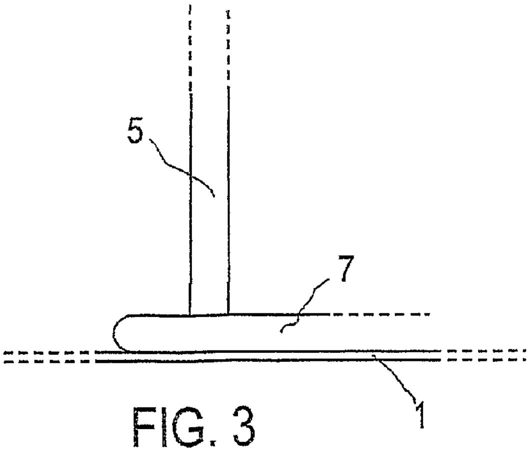
FIG. 3
FIG. 5
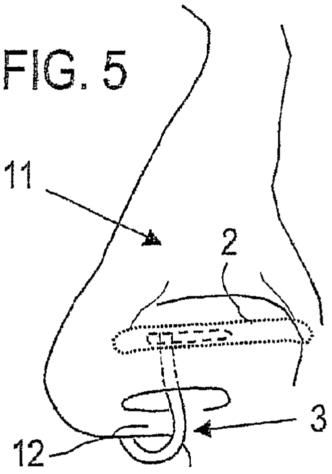

AIR FILTER FOR ENDONASAL USE

FIELD OF APPLICATION OF THE INVENTION

The present invention relates to filtering devices for environmental air, and more precisely to a device fitted inside the nose to filter the air breathed in.

REVIEW OF THE ART AT PRESENT KNOWN

Under certain conditions it is of primary importance that air from the environment should be filtered before being breathed into the lungs if more or less serious harm to the respiratory and other systems is to be avoided. Urban areas subjected to heavy automobile traffic, for example, are highly polluted by exhaust from cars and by the unburnt particles from diesel engine combustion. Other sources of air pollution occur in human activities where processes, such as transport of building materials, marble quarrying, coachwork painting and many others, produce a highly dangerous dust known as micro-particles. Even in the countryside, where these activities are not present, various forms of pollution still exist such as pollen from plants, germs, and others. Finally, domestic dust, that contains mites and often hair from the coats of animals, may be considered as a polluting agent especially in winter when heating systems are functioning. The diameters of microparticles of dust vary from 0.5 μm upwards.

Air filtering devices can be divided into two categories: filters placed where air enters closed environments and filters applied to devices worn by the person. The present invention is concerned with the second type only. Filters worn on the person include well-known forms such as facial masks of various kinds, fitted with more or less sophisticated filters according to the prevailing type of pollution. Such filters range from specialised anti-gas masks down to the simple kinds used in surgery. These latter may be considered as closest to the presently-known art that concerns this invention and should therefore be briefly described. Simple facial masks comprise a filtering component shaped to fit the lower part of the wearer's face covering the nose, mouth and chin. The filtering component is held close against nose and mouth by ties or elastic bands that are passed round the back of the head to hold the mask in place, in such a way that air is prevented from entering along the edge and must pass through the filtering material used to make the mask. Closely-woven cotton fabrics are the most popular ones for this purpose but, generally speaking, natural or synthetic materials of different weaves can be used such as non-woven fabric, cotton and other fibres, micro-porous resins, carbon granules and various salts.

Though useful for the purpose, these simple masks are somewhat unsightly and seem needless unless air pollution is so high as to make total filtering of environmental air necessary. Where pollution is not so serious it would appear prudent to assist the natural filtering function of the nasal cavity while leaving the mouth free, but this cannot be done with an ordinary mask. Devices for introducing purified air or oxygen straight into the nasal cavity exist; these consist of two plastic tubes that fit into a nasal pillow to insert inside the nostrils with a sling arrangement at the back of the head to hold the two tubes in place. Such devices however require separate filters and a supply of oxygen which makes them too bulky to be portable.

The German patent DE 668395 describes an endonasal filter having two flat capsules to be introduced into the nasal cavities, each capsule being composed of two punched coverage plates (a, b) holding a discoid filter (c) between them, the two external plates (b, b) of the two capsules are connected to each other by a flexible rib (d), wherein for every capsule the two plates (a, b) are joined together by an encircling rubber ring (e). This endonasal filter is too rigid to match with various noses, and too complicated to be really disposable The U.S. Pat. No. 2,282,681 describes an endonasal filter comprising a frame constructed from a single piece of wire and including a U shaped bridge portion, for attaching to the nose septum, having a portion of said wire extending laterally from each end thereof and looped to provide a shield in the shape of a figure 8 for supporting a filter thereon. One loop of the 8 is smaller than the other, thus tapering the shields to conform with the shape of the nasal passages at the nostrils. The two filter elements are a sort of pouches, preferably of cloth materials, with an elastic member that is sewn along the edge. They are mounted along the shields kept in a stretched condition. This endonasal filter is limited to filter elements made of materials without autonomous flexibility, so the looped ends of the connecting element are the only ones deputed to fit with the lumen of the nose channel.

SUMMARY OF THE INVENTION

Purpose of the present invention is to overcome the above drawbacks and offer an air filtering device to be applied to the nose only, a device that is not immediately noticeable and that takes up little space.

Subject of the invention is therefore an air filter as described in the claims.

According to the invention the filter comprises two essentially planar endonasal filtering components the ends of which are joined to a flexible connection that extends across the piece of cartilage between the two nostrils, similar to a spring. The essentially flat filtering components are lunette-shaped like the lumen on the channel giving access to the nasal cavities, and this form makes them adaptable to noses of different shapes because, although nostrils differ from one person to another, the lumen is fairly uniform in all cases. The surface area of one face of the filtering component is slightly greater than the area of the section at entry to the endonasal channel where it is to fit, so that it can be partially bent inwards along the edge and can fit closely against the wall of the lumen.

As regards the material to use for the filtering component, care should be taken to choose a material that is not thick enough to impede normal breathing. In this connection any person competent in the field would know which material is best to use according to the prevailing type of pollution. The filtering components are joined together by a thin U-shaped bar, its two parallel side pieces extending towards said components on which they form a roughly oval-shaped support which adheres to the filtering surfaces. For this connecting part plastic material is suitable such as transparent polyethylene, or else a thin steel wire bent to form an arch. The type of material, thickness, radius of curvature of the U-shaped arch and length of the two shanks must be such as to ensure an elastic fit against the cartilage between the nostrils and the two filtering components that must enter well inside the nostrils to intercept the lumen at entry to the nasal cavities. These requirements too can be easily satisfied from common knowledge.

The filtering device as here invented is highly practical to use. It is in no way unsightly being almost completely invisible. Production costs are extremely low. It can preferably be made in three sizes: small, medium and large. It is a device of the disposable type but can also be used several times for short periods. The life of its effectiveness as a filter depends on the concentration of polluting substances in the air; directions for use are in any case given on the package.

SHORT DESCRIPTION OF THE FIGURES

Further purposes and advantages of the present invention will be made clearer by the following detailed description of a manufactured example and by the attached drawings given for explanatory purposes in no way limited to these examples, wherein:

FIG. 1 shows a perspective view of an endonasal filter according to the present invention;

FIG. 2 shows a perspective view of a different version;

FIG. 3 shows a side view of a detail of connection between a spring for application of the filter and a filtering substrate;

FIGS. 4 and 5 show an example of how the endonasal device in FIG. 1 is fitted inside the nose.

DETAILED DESCRIPTION OF SOME PREFERRED FORMS OF REALIZING THE INVENTION

With reference to FIG. 1, it will be seen that the endonasal filter comprises two filtering components, 1 and 2, adjacent to each other, substantially flat and lunette-shaped, with between them a connecting element 3, acting as a spring. Element 3 is a single thread-like piece forming an arch, 4, the two ends of which are extended to become two parallel shanks 5 and 6 that reach as far as the two filtering components 1 and 2, and make perpendicular contact with the surfaces of said components. The shanks are then bent to form two oval-shaped elements 7 and 8 that rest on the filtering components lying closer to their inner edges than to their outer edges, and measuring about one quarter of the length of said components. The filtering components are thinner than the diameter of the thread-like arch 3, and adhere to the oval-shaped elements 7 and 8 resting on them. As far as concerns the material of the parts shown in the figure, this has already been explained above, as well as the geometrical dimensions and thicknesses.

According to a preferred form of realization, in which the connecting element 3 is made of plastic material as are the filtering components 1 and 2, said components 1 and 2 adhere to the oval-shaped elements 7 and 8 without the need for glue as it is sufficient to press them against the material while still hot in the press in order to fix them permanently.

FIG. 2 shows a variant in which, compared with the previous figure, the bases of the two shanks 5 and 6 consist of two small solid disks 9 and 10; these too can be made by moulding the same material as that of the shank, and then fixing them as above to the filtering components 1 and 2.

FIG. 3 shows how the shank 5, adhering to the filtering component 1, is bent to form oval element 7; the thicknesses shown here are close to reality. Although the filtering components 1 and 2 are so thin, the greater thickness of the oval parts 7 and 8, as well as their extension, together confer a certain degree of rigidity to the central area of filtering components 1 and 2, which helps to insert them to the required depth.

FIG. 4 illustrates an example of how the endonasal filter is applied. The figure shows the base of a nose 11, as seen from the nostrils 13 and 14, into which the two filtering components 1 and 2 have been inserted, joined by the central connecting element 3 placed across the cartilage 12 that separates the two nostrils. It will be seen that the shape of the filtering components 1 and 2 follows the outline of the nostrils 13 and 14 fairly closely and provides ample coverage when spread out.

In FIG. 5 the nose 11 is seen in profile, showing the connecting element 3 placed crosswise in relation to the cartilage 12, acting as a spring to keep the filtering components 1 and 2 in the position indicated by the dotted line. The filtering components 1 and 2 are inserted into the nostrils 13 and 14 by picking up the arch 4 between two fingers and pushing it inside the nose. This pressure widens the shanks 5 and 6 thus also altering the curve of the arch 4 which, being elastic, tends to return to its initial curve so exerting two opposing forces on the shanks 5 and 6; since these forces are both directed against the cartilage 12, the filter is thus kept in its correct position.

In the figure it will be seen that there is a slight adaptation inwards of the filtering component 2 (the same happens with component 1) as the intercepting surface is greater in relation to the section at the point of entry into the channel. This prevents unfiltered air from entering at the sides.

From the description given of a preferred realization, it is clear that changes can be made to it by competent persons without departing from the invention as described in the following claims.

The invention claimed is:

1. An endonasal filtering device for air from the environment, consisting essentially of:

two filtering components (1, 2), joined to a flexible U-shaped connection (3) with two shanks (5, 6) that extends across the piece of cartilage between the two nostrils, as a spring, wherein, said filtering components (1, 2) are essentially flat components, lunette-shaped corresponding to the lumen of the channel giving access to the nasal cavities, and said U-shaped flexible connection (3) comprises, at each end of the shank, joining means (7, 8, 9, 10) permanently fixed to the respective filtering component (1, 2), wherein, a surface area of each filtering component (1, 2) for intercepting incoming air is greater than the area of the section at entry to the endonasal channel, so as to be partially bent inwards along the edge and fit closely against the wall of the lumen of said channel, and the thickness of the flat filtering components (1, 2) is less than the thickness of the flexible connection (3).

2. The endonasal device as in claim 1, wherein, said shanks (5, 6) are substantially perpendicular to the surface of the corresponding flat filtering component (1, 2), and said joining means (7, 8, 9, 10) lie on the plane of said filtering flat components (1, 2).

3. The endonasal device as in claim 1, wherein, said joining means (7, 8, 9, 10) consist of the ends of said shanks (5, 6) curved to form a roughly oval-shaped support adhering to the surface of the filtering flat components(1, 2).

4. The endonasal device as in claim 1, wherein said joining means (7, 8, 9, 10) consist of the ends of said shanks (5, 6) flattened to form two disks (9, 10) adhering to the surface of the filtering flat components(1, 2).

5. The endonasal device as in claim 1, wherein said flexible connection (3) is made of plastic material.

6. The endonasal device as in claim 1, wherein said flexible connection (3) is made of steel wire.

7. An endonasal filtering device for air from the environment, consisting essentially of:

a flexible U-shaped connection (3) with two shanks (5, 6) configured to extend across the piece of cartilage between two nostrils; and two filtering components (1, 2) joined to the flexible U-shaped connection (3) with two shanks (5, 6), wherein, said filtering components (1, 2) are essentially flat components and are lunette-shaped corresponding to a lumen of a channel giving access to nasal cavities, and said U-shaped flexible connection (3) comprises, at an end of each shank, joining means (7, 8, 9, 10) permanently fixed to the respective filtering component (1, 2), wherein, a surface area of each filtering component (1, 2) for intercepting incoming air is greater than the area of the section at entry to the endonasal channel, so as to be partially bent inwards along the edge and fit closely against the wall of the lumen of said channel, and the thickness of the flat filtering components (1, 2) is less than the thickness of the flexible connection (3).

* * * * *